United States Patent [19]

Paaren

[11] Patent Number: 6,080,879
[45] Date of Patent: Jun. 27, 2000

[54] HEXAFLUORO-VITAMIN SYNTHESIS AND CRYSTALLIZATION METHOD, SOLVENT AND PRODUCT

[75] Inventor: Herbert E. Paaren, Madison, Wis.

[73] Assignee: Tetrionics, Inc., Madison, Wis.

[21] Appl. No.: 09/372,368

[22] Filed: Aug. 11, 1999

Related U.S. Application Data

[62] Division of application No. 09/081,106, May 19, 1998.

[51] Int. Cl.[7] .................................................. C07C 401/00
[52] U.S. Cl. ............................................................ 552/653
[58] Field of Search ............................................ 552/653

[56] References Cited

U.S. PATENT DOCUMENTS

| | | | |
|---|---|---|---|
| 4,358,406 | 11/1982 | DeLuca et al. | 260/239.55 |
| 4,391,802 | 7/1983 | Suda et al. | 424/236 |
| 4,758,383 | 7/1988 | Tachibana | 260/397.2 |
| 5,281,731 | 1/1994 | DeLuca et al. | 552/653 |
| 5,726,330 | 3/1998 | Mikami | 552/653 |
| 5,880,114 | 3/1999 | DeLuca et al. | 514/167 |
| 5,902,806 | 5/1999 | Ikeda et al. | 552/653 |

OTHER PUBLICATIONS

H.E. Paaren, H.F. DeLuca and H.K. Schnoes, *Direct C(1) Hydroxylation of Vitamin D3 and Related Compounds*, J. Org. Chem, pp. 3253–3258 (1980).

G.–D. Zhu and W.H. Okamura, *Synthesis of Vitamin D(Calciferol)*, Chemical Reviews, vol. 95, pp. 1877–1952 (1995).

D.D. Bikle, *Clinical Counterpoint: Vitamin D: New Actions, New Analogs, New Therapeutic Potential*, Endocrine Reviews, vol.13 (No. 4), pp. 765–784 (1992).

S. Jeganathan A.D. Johnston, E.A. Kuenzel, A.W. Norman and W.H. Okamura, *Thermal Rearrangement of Vinylallenes; Synthesis of 3–Deoxy–1–hydroxy–14–Epiprevitamin D3*, Journal of Organic Chemistry, vol. 49, pp. 2152–2158 (1984).

R. Bouillion et al., *Biologic Acitivity of Dihydroxylated 19–Nor–(Pre) Vitamin D3*, Journal of Bone and Mineral Research, vol. 8 (No. 8), pp. 1009–1015 (1993).

K.L. Perlman R.E. Swenson, H.E. Paaren, H.K. Schnoes and H.F. DeLuca, *Novel Synthesis of 19–NOR–VITAMIN D Compounds* Tetrahedron Letters, pp. 7663–7666 (1991).

*Primary Examiner*—Jose' G. Dees
*Assistant Examiner*—Barbara Badio
*Attorney, Agent, or Firm*—Ryndak & Lyerla

[57] ABSTRACT

This invention provides a novel synthesis and crystallization method and solvent for producing hexafluoro-vitamin D compounds, including 26, 26, 26, 27, 27, 27-hexafluoro-1α, 25-dihydroxyvitamin $D_3$. Crystalline forms of such compounds are provided that are especially suited for pharmaceutical use. Such compounds can exhibit biological activity for treating cancers, osteoporosis and psoriasis.

16 Claims, No Drawings

HEXAFLUORO-VITAMIN SYNTHESIS AND CRYSTALLIZATION METHOD, SOLVENT AND PRODUCT

This application is a divisional of U.S. application Ser. No. 09/081,106 filed May 19, 1998.

FIELD OF INVENTION

The present invention relates to fluorinated Vitamin D compounds. More particularly, the invention relates to crystalline fluorinated Vitamin D compounds, a Vitamin $D_3$ synthesis method, a solvent system and a crystallization method. More specifically, the present invention also relates to an improved method for synthesizing hexafluoro-vitamin D compounds including a method of providing such compounds in a crystalline, high purity state.

BACKGROUND OF THE INVENTION

Certain Vitamin D compounds have been demonstrated to have unique biological activity for treatment of cancers, psoriasis and osteoporosis.

The natural hormone, $1\alpha,25$-dihydroxyvitamin $D_3$, and many of the $1\alpha$-hydroxyvitamin D analogs possess a high degree of biological activity in animals and humans. As such, many vitamin D compounds are now being used or developed as pharmaceutical products to treat specific diseases such as osteoporosis, cancer, psoriasis, renal osteodystrophy, etc.

The standardized numbering system for the natural hormone, $1\alpha,25$-dihydroxyvitamin $D_3$, and 19-nor-1,25-dihydroxyvitamin $D_3$ where the 19-methylene group has been replaced with two hydrogens, is shown below in Formula (1) and Formula (2) which are as follows:

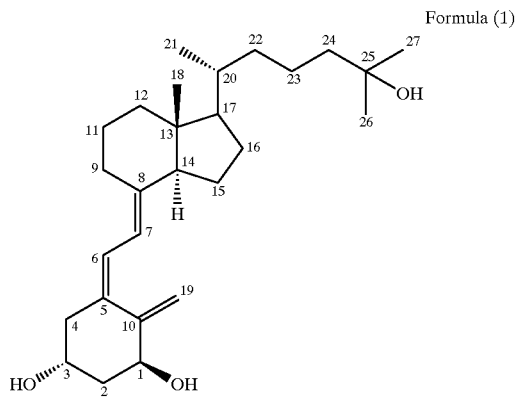

Formula (1)

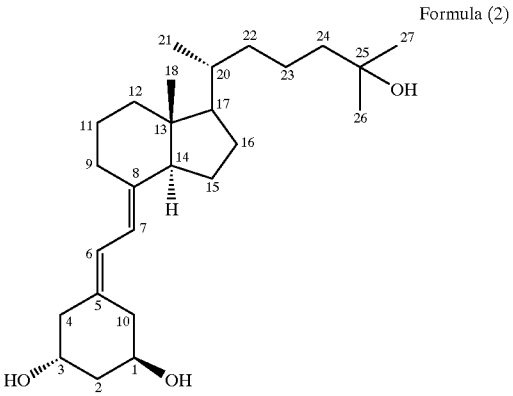

Formula (2)

Crystallization of an organic compound (or solute) requires that a solvent be chosen from which a supersaturated solution of the solute can be obtained. This ideal crystallization solvent should possess high solvent power for the substance to be crystallized at elevated temperatures and a comparatively low solvent power at room temperature or below. Heating a suspension of the organic solute in a solvent until a homogeneous solution is obtained and subsequent cooling creates a supersaturated solution from which crystallization occurs. The group of pharmaceutically useful $1\alpha$-hydroxylated vitamin D analogs possess very similar physical-chemical properties and, therefore, are normally crystallized from a very limited number of solvents, most commonly, methyl formate.

A unique group of pharmaceutically useful vitamin D analogs have fluorine atoms substituted for hydrogen atoms on a vitamin D nucleus. These fluorinated vitamin D analogs have been shown to be resistant to metabolic breakdown and possess longer therapeutic lifetimes in the body. A group of hexafluoro-$1\alpha,25$-dihydroxylated vitamin D analogs are presently being developed for the treatment of breast cancer, osteoporosis and psoriasis, and a need exists for an effective synthetic method to produce hexa-fluorovitamin compounds of the general formula:

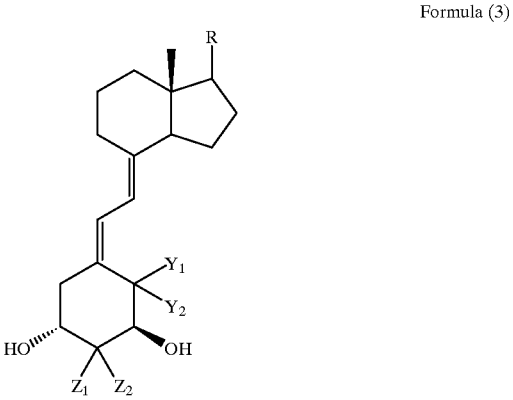

Formula (3)

Wherein the R group in the above structure represents side chains shown below where:

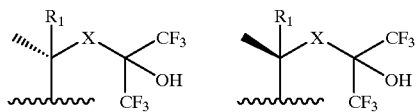

$R_1$ represents a hydrogen atom, alkyl group, hydroxy group, protected hydroxy group or alkoxy group and X represents straight, branched or cyclic hydrocarbon group, saturated or unsaturated, having 1–12 carbon atoms which may carry one or more substituents selected from, halogen, hydroxy, protected hydroxy, alkoxy or oxo groups. $Y_1$ and $Y_2$ represent hydrogen atoms or taken together represent an exocyclic methylene group $=CH_2$ and $Z_1$ and $Z_2$ which may be the same or different represent a hydrogen, alkyl, hydroxyl, protected hydroxyl or alkoxy group and taken together may represent an oxo group or $=CR_2R_3$ where $R_2$ and $R_3$ together or individually represent a hydrogen atom, alkyl group protected hydroxy group or alkoxy group.

The substitution of a fluorine atom for a hydrogen atom also greatly alters the physical-chemical properties of the molecule. In particular, the solubility of fluorinated vitamin D analogs in common organic solvents is greatly enhanced. Therefore, fluorinated vitamin D analogs are resistant to crystallization because supersaturated solutions are difficult to achieve in commonly used crystallization solvents used for vitamin D. This is especially true for the group of hexafluoro-1α, 25-dihydroxylated vitamin D analogs, depicted in the above formula, which can not be crystallized from solvents normally used in the vitamin D field. As potential pharmaceutical ingredients, it would be beneficial to be able to obtain hexafluorovitamin D compounds in crystalline form and to efficiently produce such materials in crystalline form on a commercial scale.

Generally, the crystalline form of chemical compounds are highly desirable for pharmaceutical use. Some of the advantages of active pharmaceutical compounds in crystalline form (as opposed to amorphous liquid or oil form) are that the crystalline form is generally more stable, resistant to oxidative degradation, exhibit improved handleability and, perhaps most importantly, provide a high confidence level of possessing a defined purity and potency. For example, amorphous and other noncrystalline forms of synthesized compounds can include solvents, precursors or other impurities. However, the crystalline form of such compounds inherently have a high level of purity. Consequently, it would be beneficial to be able to obtain hexafluoro-vitamin D compounds in crystalline form.

A need exists for hexafluorovitamin D analogs in crystalline form suitable for pharmacological use. A need also exists for an effective synthesis method to produce hexafluorovitamin D compounds and for a solvent to permit crystallization of such compounds.

SUMMARY OF THE INVENTION

In accordance with the present invention, hexafluorovitamin D analog compounds synthesized by the techniques described below can be crystallized by novel methodology involving the use of halogenated hydrocarbon solvents and hydrocarbon solvents in defined proportions at specified temperatures to yield highly purified stable drug products. The halogenated hydrocarbon solvents may be selected from the group of alkanes consisting of 1–6 carbons containing 1–3 halogen atoms per molecule. Examples of such solvents include, but are not limited to, methylene chloride, 1,1-dichloroethane, 1,2-dichloroethane, 1,3-dichloropropane, 1-chlorobutane, etc. The hydrocarbon solvent may be selected from a group consisting of 1–12 carbons, saturated or unsaturated, straight chain or cyclic. Examples of such solvents would be but are not limited to pentane, hexane, cyclohexane, n-heptane, etc. Preferred ratios of halogenated solvent to hydrocarbon solvent may range from 4:1 to 1:4 with the optimal ratio being determined by the nature of the chosen solvents. The preferred temperature required to dissolve the hexafluorovitamin D derivative prior to crystallization should be limited to temperatures below 60° C.

More specifically, 26,26,26,27,27,27-hexafluoro-1α,25-dihydroxyvitamin $D_3$ may be crystallized by heating the hexafluoro vitamin D compound in 1,2-dichloroethane (20 ml per gram vitamin) at 50±5° C. until a homogeneous solution is obtained. Cyclohexane (40 ml per gram vitamin) is then added and the resulting homogeneous solution is removed from the heating bath and allowed to cool to room temperature over 1.0 hour. The room temperature solution is then cooled at 5–10° C. for 4 hours and the resulting crystals isolated and air dried under aspirator vacuum for 10 min.

In accordance with the present invention, crystalline hexafluorovitamin D analog compounds are within the general Formula (3) as follows:

Formula (3)

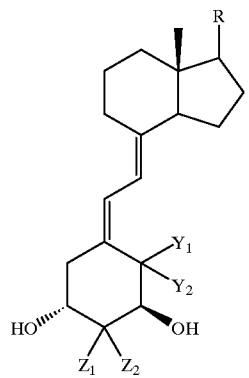

Wherein the R group in the above structure represents side chains shown below where:

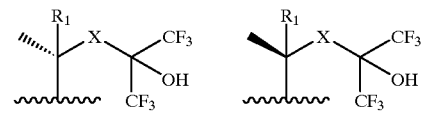

$R_1$ represents a hydrogen atom, alkyl group, hydroxy group, protected hydroxy group or alkoxy group and X represents straight, branched or cyclic hydrocarbon group, saturated or unsaturated, having 1–12 carbon atoms which may carry one or more substituents selected from, halogen, hydroxy, protected hydroxy, alkoxy or oxo groups. $Y_1$ and $Y_2$ represent hydrogen atoms or taken together represent an exocyclic methylene group $=CH_2$ and Z, and Z, which may be the same or different represent a hydrogen, alky, hydroxyl, protected hydroxyl or alkoxy group and taken together may represent an oxo group or $=CR_2R_3$ where $R_2$ and $R_3$ together or individually represent a hydrogen atom, alkyl group protected hydroxy group or alkoxy group.

As used in the description, and in the claims, the term "hydroxy-protecting group" refers to any group commonly used for the protection of hydroxy functions during subsequent reactions, including, for example, acyl or alkylsilyl groups such as trimethylsilyl, triethylsilyl, t-butyldimethylsilyl and analogous alkyl or arylsilylradicals, or alkoxyalkyl groups such as methoxymethyl, ethoxymethyl, methoxyethoxymethyl, tetrahydrofiranyl or tetrahydropyranyl. A "protected hydroxy" is a hydroxy function derivatized by one of the hydroxy-protecting groups. "Alkyl" represents a straight-chain or branched hydrocarbon radical of 1 to 10 carbons in all its isomeric forms, such as methyl, ethyl, propyl, isopropyl, butyl, isobutyl, pentyl, etc., and the terms "hydroxyalkyl", "fluoroalkyl" and "deuteroalkyl" refer to such an alkyl radical substituted by one or more hydroxy, fluoro or deuterium groups respectively. An "acyl" group is an alkanoyl group of 1 to 6 carbons in all its isomeric forms, or an aroyl group such as benzoyl, or halo-, nitro-, or alkyl substituted benzoyl groups, or an alkoxycarbonyl group of the type Alkyl—O—CO—, such as methoxycarbonyl, ethoxycarbonyl, etc., or a dicarboxylic acyl group such as oxalyl, malonyl, succinoyl, or glutaroyl. The term "aryl" signifies a phenyl-, or an alkyl-, nitro- or halo-substituted phenyl group. The term "alkoxy" signifies the group alkyl—O—.

In accordance with one aspect of the present invention, a synthesis method is provided for making hexafluoro-vitamin D compounds of formula (3).

In accordance with another aspect of the present invention, the synthesis method comprises reacting a halo-vitamin D derivative with hexafluoroacetone to yield the side chain hexafluoro-2-propanol moiety attached to the Vitamin D derivative and thereafter deprotecting the resulting Vitamin D derivative to form the hexafluorovitamin D compound. Preferably, the halo is iodo and the reaction with hexafluoroacetone as a gas or in solution. The synthesis method in accordance with the invention is suitable for forming hexafluorovitamin D compounds of formula (3) including, for example, 26, 26, 26, 27, 27, 27-hexafluoro-1α, 25-dihydroxyvitamin $D_3$ and 19-nor-1α-hydroxylated hexafluorovitamin D compounds.

In accordance with the method of crystallizing a hexafluorovitamin D compound of formula (3), the Vitamin D compound is dissolved in a solvent composed of a 1–6 carbon halogenated alkane solvent having 1–3 halogen atoms per alkane molecule and a 1–12 carbon atom hydrocarbon solvent, with a volume ratio of the halogenated alkane solvent to the hydrocarbon solvent being in the range of from about 4:1 to about 1:4 and thereafter the Vitamin D compound is crystallized. In practicing the crystallization method of the present invention, the Vitamin D compound can be first dissolved in the halogenated alkane to form a solution of the Vitamin D compound and the halogenated alkane and thereafter the hydrocarbon solvent is added to the solution to form a resulting solution composed of the Vitamin D compound in solution with the halogenated alkane and the hydrocarbon solvent.

In accordance with another aspect of the invention, a crystallization method is provided for producing hexafluorovitamin D compounds as set forth in formula (3).

In accordance with another aspect of the present invention, a method of synthesizing and crystallizing 26,26, 26, 27, 27, 27-hexafluoro-1α, 25-dihydroxyvitamin $D_3$ is provided.

In accordance with still another aspect of the present invention, hexafluoro-vitamin D compounds of formula (3) are provided in crystalline form. In accordance with another aspect of this invention, crystalline 26, 26, 26, 27, 27, 27-hexafluoro-1α, 25-dihydroxyvitamin $D_3$, 19-nor-1α, 25-dihydroxy-26, 26, 26, 27,27, 27-hexafluorovitamin $D_3$ and 2-methylene-19-nor-1α, 25-dihydroxy-26, 26, 26,27,27, 27-hexafluorovitamin $D_3$ are provided.

DETAILED DESCRIPTION OF THE INVENTION

In accordance with the present invention, methods of synthesizing the foregoing novel compounds are provided. The synthesis of 1α-hydroxylated hexafluorovitamin D analogs follow the basic cyclovitamin approach (see Paaren, H. E., DeLuca, H. F. and Schnoes, H. K., *J. Org. Chem.* (1980) 45, 3253–3258) described below in FLOW DIAGRAM I to construct the 1α-hydroxylated vitamin D nucleus.

FLOW DIAGRAM I

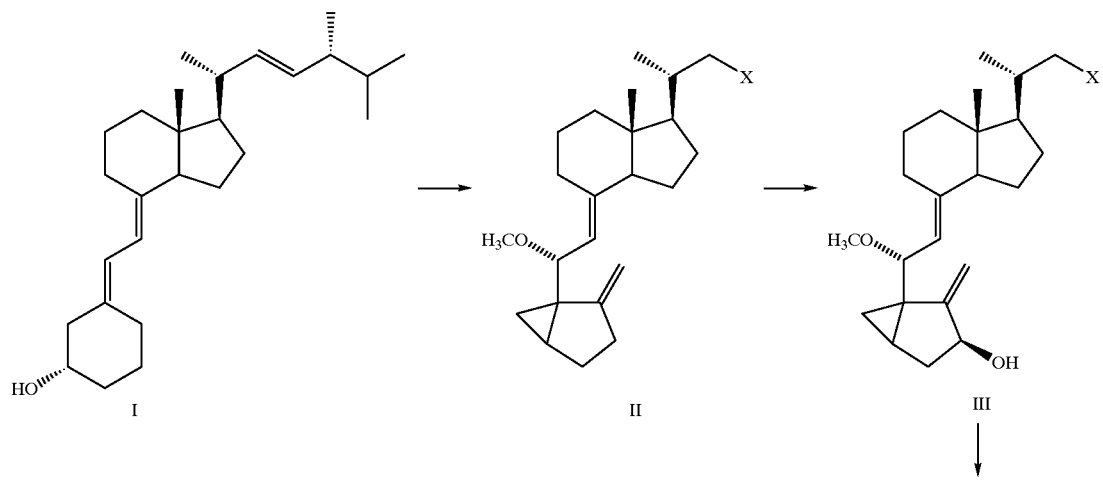

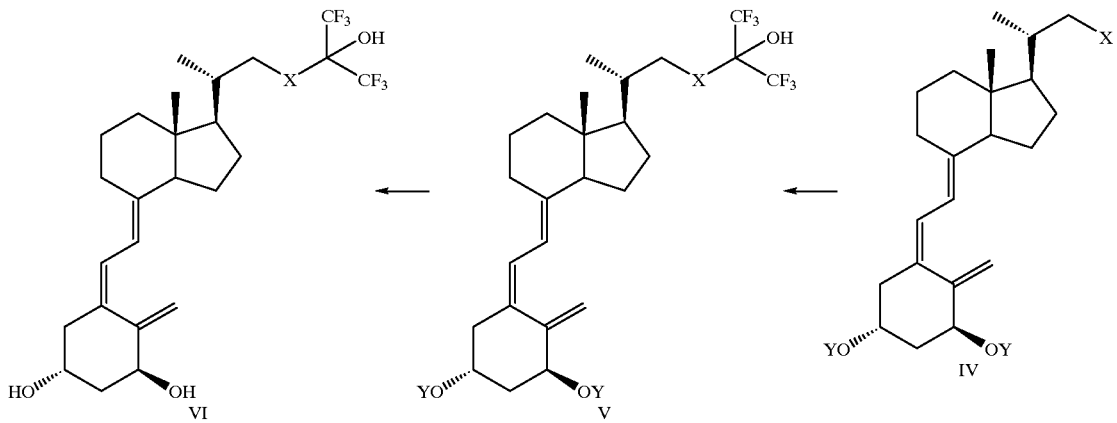

-continued

In accordance with the present invention specifically relating to the synthesis of the hexafluoro-vitamin D analogs, the functionality X in structures II–IV represents straight, branched or cyclic hydrocarbon group, saturated or unsaturated, having 1–12 carbon atoms which may carry one or more substituents selected from protected hydroxy, alkoxy or protected oxo groups. The functionality X must also terminate in a halogen atom, preferably iodine, which is capable of forming a terminal lithiated species at temperatures below −60° C., via lithium halogen exchange with alkyl lithium compounds preferably tert-butyl lithium. The lithium carbanion can then be condensed (reacted) with hexafluoroacetone as a gas or in solution to yield the side chain hexafluoro-2-propanol moiety (IV to V) thus providing a new and novel synthesis of hexafluro-1α, 25-dihydroxyvitamin D analogs as described in Example 11.

The synthetic method for producing the class of 19-nor-1α-hydroxylated hexafluoro vitamin D analog compounds is given in FLOW DIAGRAM II. Synthesis of the bicyclic ketone of Structure I where the substituent X may represent any desired group as previously defined, it being understood that any functionalities in X that might be sensitive, or that might interfere with the A-ring condensation reaction be suitably protected by methods well known in the art. Bicyclic ketones of Structure I can be prepared by known methods as documented, See, G. -D. Zhu and W. H. Okamura, *Chemical Reviews* (1995) Vol. 95, pp. 1877–1952. Preparation of 19-nor-ring-A synthons of Structure II where the Z functionality represents a group that renders the hydrogen on the adjacent carbon center sufficiently acidic to yield a reactive carbanion upon treatment with strong base. Examples of such groups are —P(O)Ph$_2$, —P(O)(OAlkyl)2, —SO2Ar or —Si(Alkyl)$_3$. Compounds of this type can be prepared by known methods as described in U.S. Pat. No. 5,281,731. Coupling of the A-ring synthon II with the bicyclic ketone I to yield the desired 19-nor-vitamin D structure III which is capable of forming a terminal side chain lithiated species, via lithium halogen exchange, that can be condensed with hexafluoroacetone to yield the side chain hexafluoroalcohol moiety as described above and in Example 11.

FLOW DIAGRAM II

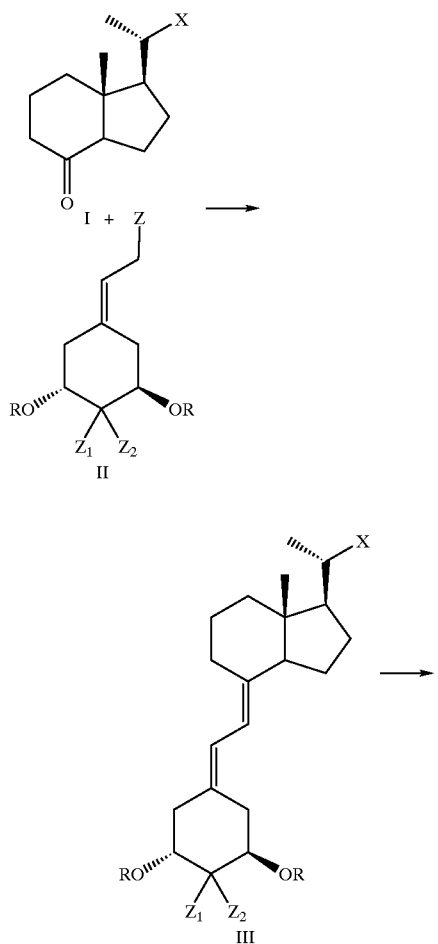

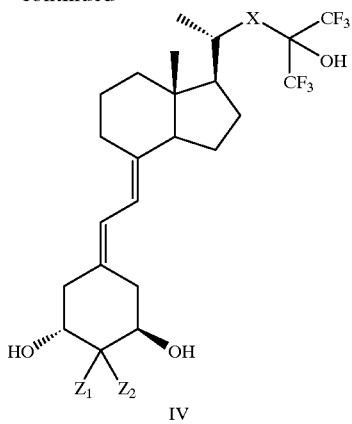

IV

This methodology represents an application of the convergent synthesis concept which has been applied for the preparation of vitamin D compounds and 19-nor-vitamin D compounds [e.g. See, G. -D. Zhu and W. H. Okamura, *Chemical Reviews* (1995) Vol. 95, pp. 1877–1952.

In accordance with another aspect of the present invention, the synthesis of hexafluoro-hydroxyvitamin D analog compounds can also be obtained from the corresponding steroid precursors. In this particular case steroids such as but not limited to cholesterol, 7-dehydrocholesterol or 1-hydroxy-7-dehydrocholesterol derivatives suitably protected and possessing the side chain functionality X as described above are converted to the side chain terminal hexafluoro-2-propanol analogs by utilizing the novel condensation reaction of hexafluoroacetone with an organolithium steroidal derivative produced by lithium halogen exchange. Subsequent conversion to the hexafluoro-vitamin D analog can be accomplished by well known and established procedures in the vitamin D field, namely, photochemical ring opening to the pre-vitamin and subsequent thermal isomerization of the pre-vitamin to the vitamin analog, for example.

In accordance with one aspect of the present invention, the synthesis of hexafluoro-hydroxyvitamin D analog compounds are described utilizing a novel condensation reaction of hexafluoroacetone with an organolithium vitamin D derivative produced by lithium halogen exchange.

A specific example of a compound in accordance with the present invention is the synthesis of 1α,25-dihydroxy-26,26,26,27,27,27-hexafluorovitamin $D_3$ shown in SCHEME I (Examples 1–12). Other examples of compounds of this type are 19-nor-1α,25-dihydroxy-26,26,26,27,27,27-hexafluorovitamin $D_3$ and 2-methylene-19-nor-1α,25-dihydroxy-26,26,26,27,27,27-hexafluorovitamin $D_3$.

In accordance with another aspect of the present invention, a method for crystallization of 1α,25-dihydroxy-26,26,26,27,27,27-hexafluorovitamin $D_3$ is given in Example 13.

EXAMPLES

Example 1

FORMATION OF 22-IODO-3,5-CYCLOVITAMIN D (2)

To a 3-neck, RB flask was added 200 ml of freshly distilled tetrahydrofuran (THF) and 44.57 g triphenylphosphine. Once the triphenylphosphine was dissolved, 29.55 g imidazole was added. When the imidazole was dissolved, the flask was cooled to −15 to −24° C. on a dry ice/acetone bath. 40.06 g iodine was added and the reaction was left to stir on the dry ice/acetone bath for 10 minutes. Then 45.12 g (1) was dissolved in 115 ml THF and was poured into the reaction flask. The dry ice/acetone bath was removed and the reaction was allowed to stir at room temperature for 35 minutes. The progress of the reaction was monitored by TLC analysis in 20% Ethyl Acetate:Hexanes ($R_f$=0.66±0.66). 164 ml saturated sodium hydrogen carbonate solution was added and the reaction was left to stir for 15 minutes. 185 ml 1M sodium sulfite was added and the reaction was concentrated to dryness on the rotovap. An extractive ethyl acetate work-up yielded 118.01 g crude (2). The material was dissolved in 100 ml 5% Ethyl Acetate:Hexanes and was filtered through 118.40 g silica in a sintered funnel. The filtrate was concentrated to dryness under vacuum to leave 48.21 g (2)—an 84% theoretical yield.

Example 2

FORMATION OF 23,23-bis(CARBOXYMETHYL)-3,5-CYCLOVITAMIN D (3)

To a 3-neck, RB flask was added 18.1 ml dimethyl malonate and 170 ml methyl sulfoxide (anhydrous). 6.7 g of sodium hydride (60% dispersion in oil) rinsed with 72 ml hexanes in a sintered funnel was carefully added to the dimethyl malonate solution. Once the reaction was homogeneous, (2) was dissolved in 160 ml tetrahydrofuran and transferred to the reaction. The reaction was heated to 55±5° C. in an oil bath for one hour, 40 minutes. Reaction progress was monitored by TLC analysis in 20% Ethyl Acetate:Hexanes ($R_f$=0.41±0.06). The reaction was removed from the oil bath and allowed to cool to room temperature. An extractive work-up with ethyl acetate yielded 49.82 g (3); a 102% theoretical yield Example 3

FORMATION OF 23-CARBOXYMETHYL-3,5-CYCLOVITAMIN D (4)

(3) was transferred to a 3-neck, RB flask with 210 ml methyl sulfoxide. 2.0 ml deionized water and 21.02 g potassium cyanide was added. The reaction was then placed on a 125±5° C. oil bath and was allowed to stir for 3 hours, 30 minutes. The progress of the reaction was monitored by TLC analysis in 20% Ethyl Acetate:Hexanes ($R_f$=0.55±0.06). The reaction was allowed to cool to room temperature and was then extracted with ethyl acetate. The ethyl acetate extract was filtered through 100 g silica in a sintered funnel with 40% Ethyl Acetate:Hexanes. The filtrate was concentrated to dryness to leave 40.86 g (4). The material was then filtered a second time through 114.88 g silica in a sintered funnel with 30% Ethyl Acetate:Hexanes. The filtrate was concentrated to dryness under vacuum to leave 37.25 g (4)—an 88% theoretical yield.

Example 4

FORMATION OF 1α-HYDROXY-23-CARBOXYMETHYL-3,5-CYCLOVITAMIN D (5)

To a 3-neck, RB flask under a steady stream of argon was added 380 ml dichloromethane (anhydrous), 5.23 g selenium (IV) oxide, and 37.5 ml tertbutylhydroperoxide butylhydroperoxide. The solution was allowed to stir for 2 hours, 15 minutes at room temperature under argon. 7.5 ml pyridine was added and the reaction was allowed to stir for another 35 minutes. Then (4) was dissolved in 265 ml dichloromethane (anhydrous) and was transferred to the reaction flask. The reaction was allowed to proceed for 45 minutes on a room temperature water bath The reaction was monitored by TLC analysis in 20% Ethyl Acetate:Hexanes ($R_f$=0.10±0.06). The reaction was then quenched with 30 g silica gel and filtered through 20 g silica gel in a sintered funnel with 50% Ethyl Acetate:Hexanes. The filtrate was concentrated to dryness under vacuum to leave 122.93 g of crude (5). The crude (5) was purified using flash chromatography with 275.40 g silica gel. The material was eluted from the silica with 30% Ethyl Acetate:Hexanes followed by 25% Ethyl Acetate:Hexanes. 200 ml fractions were collected. Fractions 3 to 10 were combined and concentrated to dryness under vacuum to leave 17.17 g purified (5)—a 44% theoretical yield.

Example 5

FORMATION OF 1α-HYDROXY-23-CARBOXYMETHYL VITAMIN D-3β-ACETATE (6)

(5) was dissolved in 190 ml acetic acid and was heated to 50±5° C. in an oil bath for 45 minutes. The flask was allowed to cool to room temperature and was then poured over 1000 ml stirring ice water to precipitate the product. The pH of the mixture as raised to 5 with 10% sodium hydroxide:water. The precipitate was then filtered and extracted with ethyl acetate. The extract was concentrated to dryness under vacuum to leave 14.75 g crude (6). The crude material (6) was purified on a 160.28 g silica flash column using 30% Ethyl Acetate:Hexanes. 125 ml fractions were collected. Fractions 4 through 7 were combined and concentrated to dryness under vacuum to yield 9.36 g purified (6)—a 51% theoretical yield.

Example 6

FORMATION OF 1α-HYDROXY-23-CARBOXYMETHYL VITAMIN D (7)

Following further purification, (6) was dissolved in 136 ml anhydrous methanol. The flask was cooled on an ice bath for 10 minutes. A solution of 2.01 g potassium carbonate in 15 ml of water was then added to the flask. After 10 minutes, the ice bath was removed and the reaction was allowed to stir at room temperature. Reaction progress was monitored by TLC analysis using 35% Ethyl Acetate:Hexanes ($R_f$=0.06±0.06). After three hours, all of the starting material was consumed. The reaction was neutralized with 1N hydrochloric acid and saturated sodium hydrogen carbonate and concentrated to dryness under vacuum. Following an extractive ethyl acetate work-up, 5.05 g of (7) (94% theoretical yield) was present Example 7

FORMATION OF 1α,3β-bis(t-BUTYLDIMETHYLSILYLOXY-23-CARBOXTHYL VITAMIN D (8)

To a 3-neck, RB flask was added 6.46 g imidazole and 23 ml dimethylformamide (anhydrous). After the imidazole was dissolved, 6.99 g t-butyldimethylsilyl chloride was added and the reaction was left to stir for 12 minutes. Then (7) was transferred to an addition funnel with 23 ml dimethylformamide and was added dropwise to the reaction mixture over 8 minutes. The reaction was allowed to stir for 16 hours, 25 minutes. The progress of the reaction towards completion was monitored by TLC analysis using 20% Ethyl Acetate:Hexanes ($R_f$=0.74±0.06). Extractive ethyl acetate work-up yielded 9.02 g (8) (125% theoretical yield).

Example 8

FORMATION OF 1α,3β-bis(t-BUTYLDIMETHYLSILYLOXY-24-HYDROXY VITAMIN D (9)

To a 3-neck, RB flask was added 180 ml ether (anhydrous) and 0.88 g powdered lithium aluminum hydride. The stirring suspension was cooled on an ice bath for 11 minutes. Then, (8) was dissolved in 65 ml ether and was transferred to an addition funnel. The addition funnel contents were added to the reaction mixture stirring on ice over 11 minutes. The reaction was then allowed to stir on ice for an additional 20 minutes. The reaction was diluted with 65 ml ether and was carefully quenched with 10% sodium hydroxide:water until white flocculent crystals were obtained. The organic solution was concentrated to dryness under vacuum to yield 7.38 g (9)—an 86% yield.

Example 9

FORMATION OF 1α,3β-bis(t-BUTYLDIMETHYLSILYLOXY-24-TOSYLOXY VITAMIN D (10)

(9) was dissolved in 30 ml pyridine (anhydrous). The flask was cooled on an ice bath for 15 minutes. 6.59g p-toluenesulfonyl chloride was then added and the reaction was allowed to stir on the ice bath for 3 hours, 30 minutes. Reaction completion was determined by TLC analysis using 20% Ethyl Acetate:Hexanes ($R_f$= 0.60±0.06). The reaction was quenched with ice, poured over stirring ice water, and filtered through celite. Following extractive ethyl acetate work-up, 6.61 g crude (10) was present. The crude material (10) was purified on a 53.32 g silica column using 5% Ethyl Acetate:Hexanes. 25 ml fractions were collected. Fractions 3 through 9 were combined and concentrated to dryness under vacuum to leave 5.34 g purified (10) (58% theoretical yield).

Example 10

FORMATION OF 1α,3β-bis(t-BUTYLDIMETHYLSILYLOXY-24-IODO VITAMIN D (11)

(10) was dissolved in 72 ml HPLC grade acetone. 4.80 g sodium iodide was added and the reaction was heated to reflux for 50 minutes until all of the starting material was consumed. Reaction progress was monitored by TLC analysis in 20% Ethyl Acetate:Hexanes ($R_f$=0.89±0.06). The reaction was then cooled in an ice bath for 10 minutes and diluted with 380 ml hexanes. The material was filtered through celite, transferred to a separatory funnel and washed with several wash solutions. The organic extract was concentrated to dryness under vacuum to leave 4.98 g crude (11). The crude material (11) was purified on a 50.20 g silica column using 20% Dichloromethane:Hexanes. 50 ml fractions were collected. Fractions 2 through 4 were combined and concentrated to dryness under vacuum to leave 5.03 g purified material (11)—a 94% yield.

Example 11

FORMATION OF 1α,3β-bis(t-BUTYLDIMETHYLSILYLOXY-26,26,26,27,27,27-HEXAFLUORO-25-HYDROXY VITAMIN D (12)

Two 3-neck, RB flasks each fitted with a stir bar, gas inlet, glass stopper, argon gas outlet, and a cannula were set up with argon running through both flasks. (11) was transferred to one of the flasks with 130 ml ether (anhydrous). To the other flask was added 32 ml ether (anhydrous).

Both of the flasks were cooled on dry ice/acetone baths for 13 minutes. To the flask containing ether, 3.13 g hexafluoroacetone was added. To the flask containing (11), 9.2 ml t-butyllithium was added. The solution containing the hexafluoroacetone was transferred to the solution containing (11) via cannula with argon flow. The reaction was allowed to stir at dry ice/acetone temperature for 30 minutes. The reaction was then quenched with water until the solution cleared and allowed to warm to room temperature. Following an extractive ether work-up, 5.26 g crude (12) remained. The crude material (12) was purified on an 80.69 g silica column using 30% Dichloromethane:Hexanes. 80 ml fractions were collected. Complete separation of the product from the impurities was not achieved. The fractions containing the product and impurities were combined and concentrated to dryness under vacuum. The material was then purified on a 20 g silica column using 35% Dichloromethane:Hexanes. 20 ml fractions were collected. Fractions 7 through 10 were combined and concentrated to dryness under vacuum to leave 3.30 g purified (12)—a theoretical yield of 66%.

Example 12

FORMATION OF 26,26,26,27,27,27-HEXAFLUORO-1α,25-DIYDROXY VITAMIN D (13)

(12) was dissolved in 20 ml freshly distilled tetrahydrofuran. 21 ml 1.0 M tetrabutyl ammonium fluoride was added and the reaction was left to stir at room temperature for 24 hours, 10 minutes. Water was then added to the reaction until the solution cleared. Following an extractive ethyl acetate work-up, 3.94 g crude (13) remained. The crude material (13) was purified on a 100.21 g silica column using 20% Acetone:Hexanes. 50 ml fractions were collected. Fractions 24 through 54 were combined and concentrated to dryness under vacuum to leave 1.81 g (13). Following an additional purification step, 1.48 g (13) was present.

Example 13

CRYSTALLIZATION OF 26,26,26,27,27,27-HEXAFLUORO-1α,25-DIHYDROXY VITAMIN D (13)

To a flask containing 1.48 g of (13) was added 30 ml of dichloroethane. The flask was heated to 50±5° C. After all of the vitamin had dissolved, 60 ml of cyclohexane was added and the flask was removed from the heating bath. After 1.0 hours, the flask was cooled to 5–10° C. for 4 hours. The crystals were then isolated and air dried under aspirator vacuum for 10 minutes to 1.31 g of(13).

| FORMULA: $C_{27}H_{38}O_3F_6$ | M.W. 524.272 |
|---|---|
| APPEARANCE: | White crystalline powder |
| MELTING RANGE: | 132–133° C. |
| UV ABSORPTION: | Maximum Abs. |
| | $(\lambda_{max}) = 264$ nm, $\epsilon = 17,100$ |
| TLC: | $R_f = 0.46$ $CH_2Cl_2$:$CH_3OH$, 9:1 |
| $^1H$ NMR: | 0.55(3H, s, 18-$CH_3$) |
| ($CDCl_3$, 500 MHz, δ) | 0.94(3H, d, J=6.1 Hz, 21-$CH_3$) |
| | 4.23(1H, m, 3-H) |
| | 4.43(1H, m, 1-H) |
| | 5.00(1H, s, 19(Z)-H) |
| | 5.33(1H, s, 19(E)-H) |
| | 6.02(1H, d, J=11.2 Hz, 7-H) |
| | 6.38(1H, d, J=11.2 Hz, 6-H) |
| MASS SPECTRUM: | m/e 524, $M^+$, $C_{27}H_{38}O_3F_6$ |
| | m/e 506, $M^+$-$H_2O$, $C_{27}H_{36}O_2$Fhd 6 |
| | m/e 488, $M^+$-$2H_2O$, $C_{27}H_{34}OF_6$ |
| | m/e 152, A-ring, $C_9H_{12}O_2$ |
| | m/e 134, A-ring-$H_2O$, $C_9H_{10}O$ |
| | m/e 69, $CF_3$ |
| RP-HPLC: | 99.84% |
| [85:15] methanol:water | Total Impurities = 0.16% |
| | Major Impurity = 0.05% |
| FT-IR (1% KBr): | 3435, 2932, 1640, 1209, 1140, |
| | 1037, 916, 693 $cm^{-1}$ |

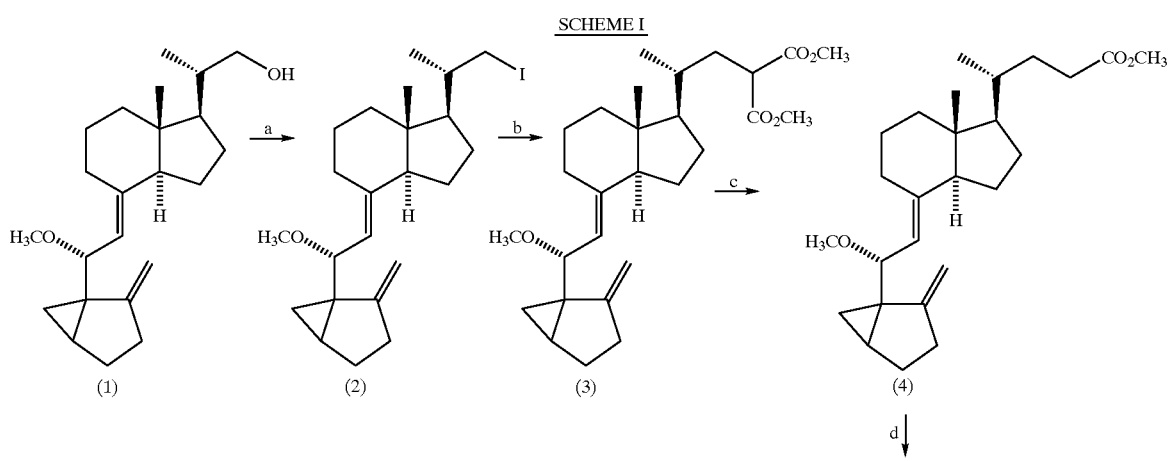

SCHEME I

-continued

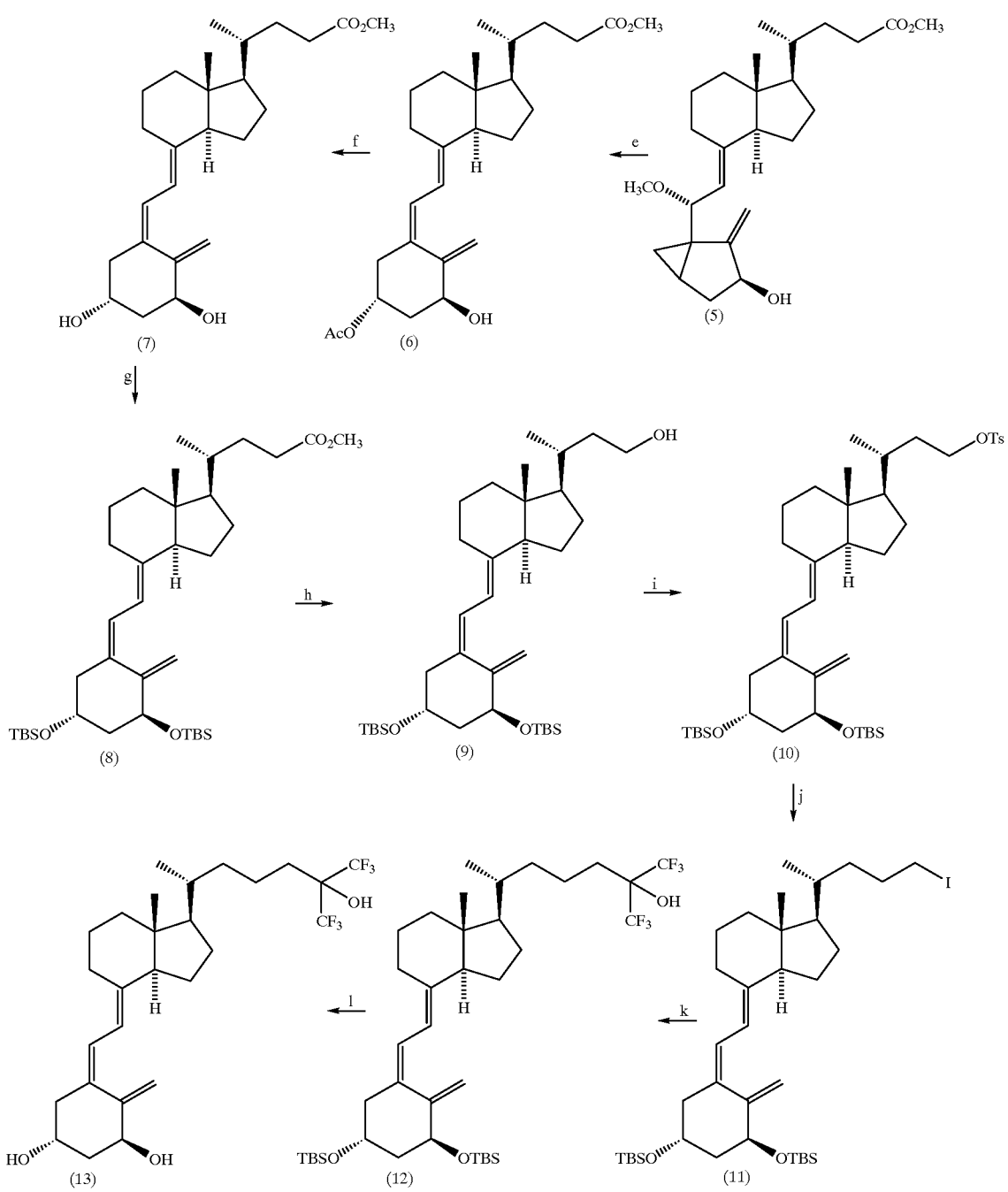

a: Ph$_3$P, I$_2$, imidazole; b: dimethylmalonate, NaH, DMSO; c: KCN, H$_2$O, DMSO;
d: SeO$_2$, t-BuOOH, pyridine; e: HOAc, 55° C.; f: K$_2$CO$_3$, CH$_3$OH, H$_2$O;
g: TBDMS-Cl, imidazole, DMF; h: LiAlH$_4$, Et$_2$O; i: TsCl, pyridine; J: NaI, acetone;
k: t-BuLi, hexafluoroacetone; l: Tetrabutylammonium fluoride, THF While the invention has been described with respect to certain preferred embodiments, it will be understood that the invention is capable of numerous changes, modifications and rearrangements without departing from the scope of the claims.

What is claimed is:

1. A method of crystallizing a hexafluoro-vitamin D compound of Formula (3)

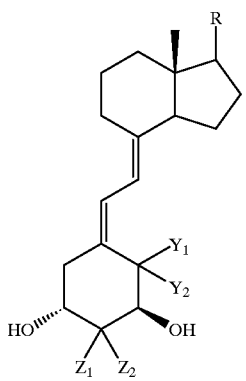

comprising:
wherein R represents

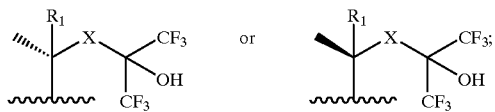

$R_1$ represents a hydrogen atom, alkyl group, hydroxy group, protected hydroxy group or alkoxy group;

X represents straight, branched or cyclic hydrocarbon group, saturated or unsaturated, having 1–12 carbon atoms which may carry one or more substituents selected from, halogen, hydroxy, protected hydroxy, alkoxy or oxo groups;

$Y_1$ and $Y_2$ represent hydrogen atoms or taken together represent an exocyclic methylene group $=CH_2$;

$Z_1$ and $Z_2$ which may be the same or different represent a hydrogen, alkyl, hydroxyl, protected hydroxyl or alkoxy group or taken together may represent an oxo group or $=CR_2R_3$ where $R_2$ and $R_3$ together or individually represent a hydrogen atom, alkyl group, protected hydroxy group or alkoxy group;

dissolving the Vitamin D compound in a solvent comprising a 1–6 carbon halogenated alkane solvent having 1–3 halogen atoms per alkane molecule and a 1–12 carbon atom hydrocarbon solvent, the volume ratio of halogenated alkane solvent to hydrocarbon solvent being in the range of from about 4:1 to about 1:4 and thereafter crystallizing the Vitamin D compound.

2. The method of claim 1, wherein said halogenated solvent is selected from the group consisting of methylene chloride, 1,1-dichloroethane, 1,2-dichloroethane, 1,3-dichloropropane, 1-chlorobutane and mixtures thereof.

3. The method of claim 1, wherein said hydrocarbon solvent is selected from the group consisting of pentane, hexane, cyclohexane, n-heptane and mixtures thereof.

4. The crystallization method of claim 1 wherein the halogenated solvent is 1,1-dichloroethane and the hydrocarbon solvent is cyclohexane.

5. The crystallization method of claim 4 wherein the volume ratio of dichloroethane to cyclohexane is about 1:2.

6. The method of claim 1 wherein the Vitamin D compound is dissolved at an elevated temperature.

7. The method of claim 1, wherein the elevated temperature is less than about 60° C.

8. The method of claim 1 wherein the Vitamin D compound is dissolved first in said halogenated alkane to form a solution of said Vitamin D compound and said halogenated alkane and thereafter said hydrocarbon solvent is added to said solution.

9. A method of obtaining a crystalline form of the hexafluorovitamin D compound 26, 26, 26, 27, 27, 27-hexafluoro-1α, 25-dihydroxyvitamin $D_3$ comprising:

dissolving the hexafluorovitamin D compound in a solvent comprising a 1–6 carbon halogenated alkane solvent having 1–3 halogen atoms per alkane molecule and a 1–12 carbon atom hydrocarbon solvent, the volume ratio of halogenated alkane solvent to hydrocarbon solvent being in the range of from about 4:1 to about 1:4 and thereafter crystallizing the Vitamin D compound.

10. The method of claim 9, wherein said halogenated solvent is selected from the group consisting of methylene chloride, 1,1-dichloroethane, 1,2-dichloroethane, 1,3-dichloropropane, 1-chlorobutane and mixtures thereof.

11. The method of claim 9, wherein said hydrocarbon solvent is selected from the group consisting of pentane, hexane, cyclohexane, n-heptane and mixtures thereof.

12. The crystallization method of claim 9 wherein the halogenated solvent is 1,1-dichloroethane and the hydrocarbon solvent is cyclohexane.

13. The crystallization method of claim 9 wherein the volume ratio of dichloroethane to cyclohexane is about 1:2.

14. The method of claim 9 wherein the Vitamin D compound is dissolved at an elevated temperature.

15. The method of claim 9, wherein the elevated temperature is less than about 60° C.

16. The method of claim 9 wherein the Vitamin D compound is dissolved first in said halogenated alkane to form a solution of said Vitamin D compound and said halogenated alkane and thereafter said hydrocarbon solvent is added to said solution.

* * * * *

UNITED STATES PATENT AND TRADEMARK OFFICE
CERTIFICATE OF CORRECTION

PATENT NO. : 6,080,879
DATED : June 27, 2000
INVENTOR(S) : Herbert E. Paaren

Page 1 of 1

It is certified that error appears in the above-identified patent and that said Letters Patent is hereby corrected as shown below:

Column 4,
Line 58, delete "Z, and Z," and insert therefor -- $Z_1$ and $Z_2$ --.

Column 5,
Line 4, delete "tetrahydrofiranyl" and insert therefor -- tetrahydrofuranyl --.

Column 7,
Lines, 35, 36, delete "hexafluro-1α,25-dihydroxyvitamin D" and insert therefor -- hexafluoro-1α,25-dihydroxyvitamin D --.
Line 53, delete "—P(O)Ph$_2$, —P(O)(OAlkyl)2," and insert therefor -- —P(O)Ph$_2$, —P(O)(OAlkyl)$_2$, --.

Column 10,
Line 63, delete "butylhydroperoxide".

Column 11,
Line 2, after "bath" insert a period.
Line 54, delete "BUTYLDIMETHYLSILYLOXY-23-CARBOXTHYL" and insert therefor -- BUTYLDIMETHYLSILYLOXY-23-CARBOXYMETHYL --.

Column 13,
Line 25, delete "25-DIYDROXY" and insert therefor -- 25-DIHYDROXY --.

Column 14,
Line 29, delete "m/e 506, M$^+$ - H$_2$O, C$_{27}$H$_{36}$O$_2$Fhd$_6$" and insert therefor -- m/e 506, M$^+$ - H$_2$O, C$_{27}$H$_{36}$O$_2$F$_6$ --

Signed and Sealed this

Twenty-sixth Day of February, 2002

Attest:

*Attesting Officer*

JAMES E. ROGAN
*Director of the United States Patent and Trademark Office*